US010993894B2

(12) United States Patent
Gambogi et al.

(10) Patent No.: US 10,993,894 B2
(45) Date of Patent: *May 4, 2021

(54) METHODS OF PREPARING NON-ALCOHOL BIOACTIVE ESSENTIAL OIL MOUTH RINSES

(71) Applicant: Johnson & Johnson Consumer Inc., Skillman, NJ (US)

(72) Inventors: Robert Gambogi, Hillsborough, NJ (US); Carolyn J. Mordas, Ewing, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/542,533

(22) Filed: Aug. 16, 2019

(65) Prior Publication Data
US 2019/0365618 A1 Dec. 5, 2019
US 2021/0085578 A9 Mar. 25, 2021

Related U.S. Application Data

(60) Continuation of application No. 15/668,775, filed on Aug. 4, 2017, now Pat. No. 10,434,050, which is a division of application No. 15/487,913, filed on Apr. 14, 2017, now Pat. No. 9,763,863, which is a continuation of application No. 14/326,041, filed on Jul. 8, 2014, now Pat. No. 9,693,944, which is a division of application No. 12/827,970, filed on Jun. 30, 2010, now abandoned.

(51) Int. Cl.
*A61K 8/34* (2006.01)
*A61K 8/368* (2006.01)
*A61K 8/39* (2006.01)
*A61K 8/46* (2006.01)
*A61K 8/90* (2006.01)
*A61Q 11/00* (2006.01)
*A61K 8/37* (2006.01)
*A61K 8/49* (2006.01)
*A61K 8/86* (2006.01)
*A61K 8/92* (2006.01)

(52) U.S. Cl.
CPC .............. *A61K 8/345* (2013.01); *A61K 8/34* (2013.01); *A61K 8/347* (2013.01); *A61K 8/368* (2013.01); *A61K 8/37* (2013.01); *A61K 8/39* (2013.01); *A61K 8/463* (2013.01); *A61K 8/498* (2013.01); *A61K 8/4973* (2013.01); *A61K 8/86* (2013.01); *A61K 8/90* (2013.01); *A61K 8/922* (2013.01); *A61Q 11/00* (2013.01); *A61K 2800/30* (2013.01); *A61K 2800/74* (2013.01); *A61K 2800/92* (2013.01)

(58) Field of Classification Search
CPC .......... A61K 8/345; A61K 8/34; A61K 8/368; A61K 8/347; A61K 8/86; A61K 8/37; A61K 8/922; A61K 8/4973; A61K 8/498; A61K 8/463; A61K 8/39; A61K 8/90; A61K 2800/30; A61K 2800/74; A61K 2800/92; A61Q 11/00; A61P 1/02

See application file for complete search history.

(56) References Cited

U.S. PATENT DOCUMENTS

| 3,277,132 A | 10/1966 | Wild et al. |
| 3,639,570 A * | 2/1972 | Becker ................. C11D 3/3703 424/54 |
| 3,959,458 A | 5/1976 | Agricola |
| 4,051,234 A | 9/1977 | Gieske |
| 4,150,151 A | 4/1979 | Pader |
| 4,411,813 A | 10/1983 | Voisin |
| 4,547,361 A | 10/1985 | Steltenkamp et al. |
| 4,894,220 A | 1/1990 | Nabi |
| 4,945,087 A | 7/1990 | Talwar |
| 5,190,747 A | 3/1993 | Sekiguchi |
| 5,283,056 A | 2/1994 | Chung |
| 5,284,648 A | 2/1994 | White |
| 5,292,527 A | 3/1994 | Konopa |
| 5,320,863 A | 6/1994 | Chung |
| 5,328,682 A | 7/1994 | Pullen et al. |
| 5,407,662 A | 4/1995 | Mackles |
| 5,466,437 A | 11/1995 | Gaffar |
| 5,681,548 A | 10/1997 | Esposito |
| 5,707,610 A | 1/1998 | Ibsen |
| 5,723,106 A | 3/1998 | Buch |
| 5,733,530 A | 3/1998 | Bacca |
| 5,817,295 A * | 10/1998 | Chaudhari ............... A61K 8/34 424/49 |
| 5,817,297 A | 10/1998 | Ha |
| 5,891,422 A | 4/1999 | Pan et al. |
| 5,945,087 A | 8/1999 | Nelson |
| 5,985,177 A | 11/1999 | Yoshida et al. |
| 6,045,813 A | 4/2000 | Ferguson |
| 6,106,815 A | 8/2000 | Kang |
| 6,121,315 A | 9/2000 | Nair |
| 6,261,540 B1 | 7/2001 | Nelson |
| 6,348,187 B1 | 2/2002 | Pan |
| 6,416,745 B1 | 7/2002 | Markowitz |
| 6,585,961 B1 | 7/2003 | Stockel |

(Continued)

FOREIGN PATENT DOCUMENTS

| JP | 2009096724 A | 5/2009 |
| WO | WO 1996016633 A1 | 6/1996 |

(Continued)

*Primary Examiner* — Snigdha Maewall

(57) ABSTRACT

The invention relates generally to liquids such as mouth rinses for the prevention and elimination of bad breath as well as for the reduction of oral microorganisms responsible for the development of dental plaque and tooth decay. In particular, the present invention relates to a method of preparing non-alcohol or reduced alcohol mouth rinses effective at preventing the above-mentioned problems.

9 Claims, No Drawings

(56) References Cited

U.S. PATENT DOCUMENTS

| | | |
|---|---|---|
| 6,682,722 B2 | 1/2004 | Majeti |
| 6,797,683 B2 | 9/2004 | Shana'a |
| 7,084,104 B2 | 8/2006 | Martin |
| 7,087,650 B2 | 8/2006 | Lennon |
| 2003/0171231 A1 | 9/2003 | Shana et al. |
| 2004/0047822 A1 | 3/2004 | Zamudo Tena |
| 2005/0014827 A1 | 1/2005 | Schur |
| 2005/0100597 A1* | 5/2005 | Pinza .................. A61P 1/02 424/464 |
| 2006/0013778 A1 | 1/2006 | Hodosh |
| 2006/0093691 A1 | 5/2006 | Thurot et al. |
| 2006/0105000 A1 | 5/2006 | Friedman |
| 2008/0020024 A1 | 1/2008 | Kulkarni et al. |
| 2008/0038210 A1 | 2/2008 | Yano |
| 2008/0085246 A1 | 4/2008 | Rabenhorst |
| 2008/0171089 A1 | 7/2008 | Blondino |
| 2008/0219935 A1 | 9/2008 | Kwak |
| 2008/0247966 A1 | 10/2008 | Natsch |
| 2008/0247972 A1 | 10/2008 | Conceicao |
| 2010/0189663 A1 | 7/2010 | Gallis |
| 2011/0070306 A1 | 3/2011 | Baker, Jr. |

FOREIGN PATENT DOCUMENTS

| | | |
|---|---|---|
| WO | WO 1997030685 A1 | 8/1997 |
| WO | WO 1998040094 A1 | 9/1998 |
| WO | WO 2008016837 A2 | 2/2008 |
| WO | WO 2009019604 A2 | 2/2009 |

* cited by examiner

METHODS OF PREPARING NON-ALCOHOL BIOACTIVE ESSENTIAL OIL MOUTH RINSES

CROSS REFERENCE TO RELATED APPLICATIONS

The present application is a continuation application which claims the benefit of divisional application Ser. No. 15/668,775, filed Aug. 4, 2017, which claims the benefit of Ser. No. 15/487,913, filed Apr. 14, 2017 (now U.S. Pat. No. 9,763,863, Granted Sep. 19, 2017), which is continuation application of United States divisional patent application Ser. No. 14/326,041, filed Jul. 8, 2014 (now U.S. Pat. No. 9,693,944, Granted Jul. 4, 2017), which application claims the benefit of U.S. non-provisional application Ser. No. 12/827,970 filed Jun. 30, 2010 (abandoned), the complete disclosure of which is incorporated herein by reference for all purposes.

FIELD OF THE INVENTION

The invention relates generally to liquids such as mouth rinses for the prevention and elimination of bad breath as well as for the reduction of oral microorganisms responsible for the development of dental plaque and tooth decay. In particular, the present invention relates to methods of preparing non-alcohol or reduced alcohol mouth rinses effective at preventing the above-mentioned problems.

BACKGROUND OF THE INVENTION

Mouth rinse or mouthwash compositions have been used by people for many years for the prevention of bad breath and for the elimination of bacteria and other oral microorganisms that are responsible not only for bad breath but also tooth decay, plaque and gum diseases such as gingivitis and periodontitis. To this end, antiseptic mouthwashes in the past have been designed to clean the oral cavity, provide fresh breath and kill these pathogenic microbes.

Leading antiseptic mouth rinses have traditionally contained alcohol (i.e., ethanol) at fairly high levels, ranging from approximately 20% up to about 30% by volume, based on the total mouthwash volume (hereinafter referred to as "% v/v"). Alcohol is used both as a vehicle and as a solvent in which the active ingredients, and additives such as astringents, fluorides, color additives, flavor oils, and the like, can be dissolved and then dispersed into solution. Alcohol also provides a preservative role for the mouth rinse during storage and use, and enhances the flavor oil organoleptic cues.

However, the use of high levels of alcohol may sometimes be found unacceptable by some mouthwash users. Senior citizens have also complained about problems related to gargling with such mouth rinses, and chronic exposure has been found to result in a feeling of gum "burn" resulting from the high concentrations of alcohol. It has also been reported that alcoholic mouth rinses can result in an unpleasant "dry mouth" sensation.

On the other hand, reducing the levels of alcohol in these mouth rinse compositions can have significant disadvantages. Such disadvantages include a reduction in the solubility of the mouth rinse actives and/or the other mouth rinse ingredients.

For example, it has been found that lowering alcohol concentration (i.e., replacing the alcohol with water) in commercially available mouth rinse compositions can result in cloudy or turbid compositions. Cloudy or turbid compositions present a clear disadvantage from an aesthetic point of view since clear mouth rinse solutions are certainly more preferred by consumers than cloudy, turbid or otherwise heterogeneous ones.

Additionally, it has been found that lower alcohol concentrations result in a noticeable decrease in the ability of the composition to kill the oral microorganisms responsible for bad breath, plaque and gum disease. This loss in antimicrobial activity is not only due to the reduction of alcohol as a vehicle, but also to the reduced bioavailability of the solubilized actives.

Thymol, for example, is a well known antiseptic compound, also known as an essential oil, which is utilized for its antimicrobial activity in a variety of mouthwash or mouth rinse preparations. In particular, thymol can be utilized in oral hygiene compositions such as mouth rinses in sufficient quantities to provide desired beneficial therapeutic effects. Mouthwashes with thymol are well-known, and have been used by millions of people for over one hundred years. They have been proven effective in killing microbes in the oral cavity that are responsible for plaque, gingivitis and bad breath. Thymol, together with other essential oils such as methyl salicylate, menthol and eucalyptol, comprise the active component in some antiseptic mouth rinses. These oils achieve good efficacy although present in small amounts. Without being restricted to any specific theory, it is now believed that the efficacy and taste of antiseptic mouth rinses may be due to the improved dispersion or dissolution of the oils and bioavailability after such dispersion or dissolution of these four active ingredients.

Obviously then, there is a substantial need for the development of a reduced and/or no alcohol mouth rinses, and methods of producing them or other liquids, which are aesthetically pleasing to consumers and provide improved dispersion or dissolution of the essential oils yet maintain the bioavailability of the essential oils for preventing bad breath, killing oral microbes and reducing or eliminating plaque.

Therefore, an aspect of the present invention is to liquid compositions containing oil or oily components which have reduced turbidity or cloudiness.

Another aspect of the present invention is to provide mouth rinse compositions which are aesthetically pleasing to consumers and provide improved dispersion or dissolution of the essential oils yet maintain the bioavailability of the essential oils for preventing bad breath, killing oral microbes and reducing or eliminating plaque.

SUMMARY OF THE INVENTION

In certain embodiments, the present invention relates to methods for preparing a liquid composition or mouth rinse comprising the steps of:
a.) preparing a first premix composition comprising:
   i. a first oil or oily component;
   ii. optionally, a first polyol solvent, and
   iii. optionally, a flavor;
b.) preparing a second premix composition comprising:
   i. a second oil or oily component having a degree of hydrophobicity less than the degree of hydrophobicity of the first oil or oily component, and
   ii. a second polyol solvent;
c.) preparing a third premix composition comprising:
   i. at least one surfactant, and
   ii. an aqueous phase comprising water;
d.) adding the first premix to the third premix;

e.) mixing the composition of step d.) until uniform and homogeneous;

f.) adding the second premix to the composition of step e.) and mixing until uniform and homogeneous;

g.) optionally, adding a sugar alcohol solvent; and h.) optionally, mixing the composition of step g.) until uniform and homogeneous.

In certain embodiments, the liquid composition or mouth rinse is a reduced alcohol or non-alcohol composition.

In further embodiments, a method for preparing a reduced alcohol or non-alcohol, antimicrobial mouth rinse composition is disclosed that exhibits a high level of antimicrobial activity as measured by an M-factor greater than 0.5 (or about 0.5), optionally 1.0 (or about 1.0) optionally, 2.0 (or about 2.0), or optionally 3.0 (or about 3.0) where "M-factor" equals the log RLU value of biofilm treated with water used as the negative control minus the log RLU value of biofilm treated with the mouth rinse composition being tested. In addition, the oral mouth rinse compositions of this invention are clear (to the unaided human eye) and aesthetically appealing products.

DETAILED DESCRIPTION OF THE INVENTION

The liquid or mouth rinse compositions of the present invention can comprise, consist of, or consist essentially of the essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The reduced alcohol or non-alcohol mouthwash and mouth rinse compositions described herein provide an anti-microbially effective amount of one or more antimicrobial essential oils towards oral microorganisms responsible for oral malodor and the build-up of plaque and calculus and the resulting tooth and gum diseases that may follow.

The phrase "antimicrobially effective amount" means the concentration or quantity or level of the compound of the present invention that can attain a particular medical end in having toxic activity for oral microorganisms.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

All percentages, parts and ratios are based upon the total weight of the composition of the present invention, unless otherwise specified. All such weights as they pertain to the listed ingredients are based on the level of the particular ingredient described and, therefore, do not include carriers or by-products that may be included in commercially available materials, unless otherwise specified.

The phrase "reduced alcohol" or "reduced level of alcohol" indicates that the liquid compositions are essentially free of alcohol which means the liquid compositions or mouth rinses of the present invention contain an amount of a $C_2$-$C_4$ monohydric alcohol of up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total composition. Optionally, the compositions of the present invention are free of $C_2$-$C_4$ monohydric alcohols.

The term "sterile water", as used herein, means sterile water for irrigation/injection U.S.P. The USP designation means that the sterile water for irrigation/injection is the subject of an official monograph in the current (as of the filing date of this application) US Pharmacopeia.

Unless otherwise specified, the phrase "oil(s) or "oily component(s)" means any hydrophobic, water immiscible compound, including but not limited to, essential oils (such as menthol, thymol, eucalyptol and methyl salicylate), other flavor oils, unsaturated aliphatic long chain alcohols and/or aldehydes such as 1-decen-3-ol; cis-2-nonen-1-ol, trans-2-decenal and mixtures thereof, other hydrophobic compounds such as organic acids, vitamin E, vitamin E acetate, apigenin, triclosan and mixtures thereof and mixtures of any of the above disclosed hydrophobic, water immiscible compounds.

The terms "hydrophobic", "hydrophobicity" or "degree of hydrophobicity" of an oil or oily component of the present invention or any mixture of such oil or oily components is represented by the Octanol Water Partition Coefficient ($K_{ow}$). $K_{ow}$ is the ratio of the concentration by weight of an oil or oily component in the octanol phase and the concentration by weight of the oil or oily component in water phase at equilibrium and at a specified temperature for the biphasic octanol and water system. The logarithm of $K_{ow}$ is called the log P. The experimental values used to calculate the $K_{ow}$ are typically measured at a temperature of between 20° C. to 25° C.

Alternatively, the log P values are conveniently calculated by the "C LOG P" program, also available from Daylight CIS. This program also lists experimental log P values when they are available in the Pomona92 database. The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each oil or oily component, and takes into account the numbers and types of atoms, the atom connectivity, and chemical bonding. The C log P values, which is considered reliable and a widely used estimate for this physicochemical property, can be used instead of the experimental $K_{ow}$ method for measuring log P values.

The higher the log P of the oil or oily component, the more hydrophobic (or, the greater the degree of hydrophobicity of) the oil or oily component.

The term "turbidity" as used herein means the cloudiness or haziness of a fluid caused by individual particles (suspended solids or liquids) that are generally invisible to the unaided eye. Fluids can contain suspended solid or liquid matter consisting of varying particle size. While some suspended material will be large enough and heavy enough to settle rapidly to the bottom of the container (or separate into distinct layers) if a liquid sample is left to stand, very small particles will settle (or separate out) only very slowly or not at all if the sample is regularly agitated or the particles are colloidal. These small solid or liquid particles cause the liquid to appear turbid.

One property of such particles is that they will scatter a light beam focused on them. This light scattering effect is considered a good measure of turbidity in water. Turbidity measured this way uses an instrument called a Turbidimeter with the detector setup to the side of the light beam. The more particles floating in water, the more light is scattered toward the detector and the higher the value of detected light. A lower value of detected light indicates a clearer or less cloudy solution. The units of turbidity from a calibrated Turbidimeter are called Nephelometric Turbidity Units (NTUs). A clear formulation is defined as a formulation with an NTU of less than 12 (or about 12).

First Premix Composition

The liquid or mouth rinse compositions of the present invention comprise a first premix composition.

In certain embodiments, the first premix composition includes a first oil or oily component and a first polyol solvent.

First Oil or Oily Component

The first premix composition of the present invention comprises a first oil or oily component, the first oil or oily component being any oil or oily component or mixture of such oil or oily components. In certain embodiments, the first oil or oily component has a log P of no less than or greater than 2.1 (or about 2.1), optionally 2.2 (or about 2.2). In certain embodiments such as certain mouth rinse embodiments, the first oil or oily component of the present invention comprises at least one antimicrobial essential oil.

Antimicrobial Essential Oils

In certain embodiments, the enhanced antimicrobial efficacy of non-alcohol mouth rinse compositions as described herein is attributed to the presence of minor amounts of one or more antimicrobial or bioactive essential oils (i.e. thymol, eucalyptol, menthol and methyl salicylate).

Thymol, $[(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses. Methyl salicylate, $[C_6H_4OHCOOCH_3$, also known as wintergreen oil], additionally provides flavoring to the together with its antimicrobial function. Eucalyptol ($C_{10}H_{18}O$, also known as cineol) is a terpene ether and provides a cooling, spicy taste. Eucalyptol may be used in place of thymol in certain formulations in the same amount if desired. Menthol $(CH_3C_6H_9(C_3H_7)OH)$, also known as hexahydrothymol is also only slightly soluble in alcohol, and is fairly volatile. Menthol, in addition to any antiseptic properties, provides a cooling, tingling sensation.

In certain embodiments, the essential oils are used in amounts effective to provide antimicrobial activity in the oral cavity. In specific embodiments, the total amount of essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contain thymol and additionally eucalyptol, menthol, or methyl salicylate, or mixtures thereof. Optionally, the composition contains all four of these essential oils.

In certain embodiments, thymol is employed in amounts of from 0.001% (or about 0.001%) to 0.25% (or about 0.25%) w/v, or optionally from 0.04% (or about 0.04%) to 0.07% (or about 0.07%) w/v of the composition. In certain embodiments, eucalyptol may be employed in amounts of from 0.001% (or about 0.001%) to 0.11% (or about 0.11%) w/v, or optionally from 0.085% (or about 0.085%) to 0.10% (or about 0.10%) w/v of the composition. In certain embodiments, menthol is employed in amounts of from 0.001% (or about 0.001%) to 0.25% (or about 0.25%) w/v, or optionally from 0.035% (or about 0.035%) to 0.05% (or about 0.05%) w/v of the composition. In certain embodiments, methyl salicylate is employed in amounts of from 0.001% (or about 0.001%) to 0.08% (or about 0.08%) w/v, or optionally from 0.04% (or about 0.04%) to 0.07% (or about 0.07%) w/v of the composition.

In some embodiments, the carrier for the essential oils (the active ingredients) is typically a water-alcohol mixture, generally water-ethanol. In the past, some antiseptic oral mouth rinse compositions, required ethanol levels of up to about 27% v/v. These high levels were necessary to assist the actives in providing the necessary antimicrobial functionality as well as providing a clear, aesthetically attractive liquid medium. Merely reducing the alcohol levels, without the addition of other formulation components, results in a cloudy, less efficacious product.

Without being bound to any theory, it is believed that in these high alcohol level oral compositions, the alcohol solubilizes the antimicrobial essential oils and in so doing acts to keep the essential oils bioactive. The antimicrobial essential oils are more readily dispersed throughout the solution and remain free or unbound to attack pathogenic microbes throughout the oral cavity. Reducing the alcohol levels was believed to adversely affect this enhancement mechanism. In accordance with the present invention, however, it was surprisingly and unexpectedly found that the level of alcohol can be reduced or eliminated without sacrificing antimicrobial efficacy or clarity if the mouth rinse composition contains a solvent system and surfactants as taught herein.

First Polyol Solvent

In certain embodiments, a first polyol solvent is added to the first premix composition. The first polyol solvent comprises a polyol or polyhydric alcohol selected from the group consisting of polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 0% to 20.0% (or about 20.0%) w/v, optionally from 1.0% (or about 1.0%) to 15.0% (or about 15.0%) w/v, or optionally from 2.5% (or about 2.5%) to 8.0% (or about 8.0%) w/v of the composition.

Flavors or Flavorants

In certain embodiments, the first premix composition further comprises flavors or flavorants may to modify or magnify the taste of the liquid composition or mouth rinse, or reduce or mask the sharp "bite" or "burn" of ingredients such as thymol. Suitable flavors include, but are not limited to, oil of anise, anethole, benzyl alcohol, spearmint oil, citrus oils, vanillin and the like may be incorporated. In these embodiments, the amount of flavor oil added to the composition can be from 0.001% (or about 0.001%) to 1.0% (or about 1.0%) w/v, or optionally from 0.01% (or about 0.010%) to 0.30% (or about 0.30%) w/v of the total composition.

The particular flavors or flavorants, and other taste-improving ingredients, employed will vary depending upon the particular taste and feel desired. Those skilled in the art can select and customize these types of ingredients to provide the desired results.

Second Premix Composition

The compositions of the present invention further comprise a second premix composition.

In certain embodiments, the second premix composition comprises a water insoluble component and a second solvent or solvent system comprising, consisting of or consisting essentially of at least one polyol solvent.

Second Oil or Oily Component

The second premix composition of the present invention comprises a second oil or oily component, the second oil or oily component being any oil or oily component or mixture of such oil or oily components such that the hydrophobicity (or degree of hydrophobicity) of the second oil or oily component is less than the hydrophobicity (or degree of hydrophobicity) of the first oil or oily component. In certain embodiments, the second oil or oily component has a log P of no more than or less than 2.1 (or about 2.1), optionally 2.0 (or about 2.0). In certain embodiments, the second oil or oily component of the present invention is or comprises at least one organic acid. In certain embodiments, the organic acid is used as a buffer or part of a buffering system.

Organic Acid

Organic acids suitable for use in the compositions of the present invention include, but are not limited to, ascorbic acid, sorbic acid, citric acid, glycolic acid, lactic acid and acetic acid, benzoic acid, salicylic acid, phthalic acid, phenolsulphonic acid, succinic acid and mixtures thereof, optionally, the organic acid is selected from the group consisting of benzoic acid, sorbic acid, succinic acid, citric acid and mixtures thereof, or optionally, the organic acid is benzoic acid. In certain embodiment, the organic acid buffer is present in amounts of from 0.001% (or about 0.001% w/v) to 1.0% w/v (or about 1.0% w/v) of the composition.

When used as buffers or as part of a buffering system, the organic acids are incorporated in amounts that maintain the pH at levels of from 3.0 (or about 3.0) to 8.0 (or about 8.0), optionally from 3.5 (or about 3.5) to 6.5 (or about 6.5), optionally from 3.5 (or about 3.5) to 5.0 (or about 5.0). Without being limited any theory, it is believed that these pH levels provide the essential oils with an environment that also maximizes their antimicrobial activity and promotes stability.

In certain embodiments, the total amount of any oil or oily components present in the disclosed compositions of the present invention should not exceed 1.35% w/v (or about 1.35% w/v) of the total composition. Optionally, the total of all oil or oily components, can be present in an amount of from 0.04% (or about 0.04%) to 1.35% (or about 1.35%) w/v, or optionally from 0.10% (or about 0.10%) to 0.4% (or about 0.4%) w/v of the total composition.

Second Polyol Solvent

A second polyol solvent is added to the second premix. In certain embodiments, the second polyol solvent can be the same as or different from the first polyol solvent and comprises a polyol or polyhydric alcohol selected from the group consisting of polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 1% (or about 1%) to 15.0% (or about 15.0%) w/v, or optionally from 2.5% (or about 2.5%) to 8.0% (or about 8.0%) w/v of the composition.

In certain embodiments, where a first polyol solvent is not added to the first premix, the second polyol solvent can be present in an amount of from 1.0% (or about 1.0%) to 30.0% (or about 30.0%) w/v, or optionally from 5.0% (or about 5.0%) to 15.0% (or about 15.0%) w/v of the composition.

Third Premix Composition

The compositions of the present invention further comprise a third premix composition. In certain embodiments, the third premix composition comprises a surfactant and in an aqueous phase.

Surfactant

Suitable examples of surfactants useful in the compositions of the present invention include anionic surfactants, nonionic surfactants, amphoteric surfactants and mixtures thereof.

Anionic surfactants useful herein include, but are not limited to, sarcosine type surfactants or sarcosinates; taurates such as sodium methyl cocoyl taurate; alkyl sulfates such as sodium trideceth sulfate or sodium lauryl sulfate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; block copolymers such as ethylene oxide and propylene oxide copolymers e.g. Poloxamers; ethoxylated hydrogenated castor oils available commercially for example under the trade name CRODURET (Croda Inc., Edison, N.J.); Alkyl polyethylene oxide e.g. Polysorbates, and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the liquid or mouth rinse compositions contain at least one alkyl sulfate surfactant either alone or in addition to at least one of the other above mentioned surfactants. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. A typical percentage breakdown of alkyl sulfates by alkyl chain length in commercially available sodium lauryl sulfate (SLS) is as follows:

| Alkyl Chain Length | Component Percentage in SLS |
| --- | --- |
| $C_{12}$ | >60% |
| $C_{14}$ | 20%-35% |
| $C_{16}$ | <10% |
| $C_{10}$ | <1% |
| $C_{18}$ | <1% |

Suitable commercially available mixtures include Stepanol WA-100 NF USP, (Stepan, Northfield, Ill.), Texapon K12 G PH, (Texapon, Cognis, Germany) and mixtures thereof.

In certain embodiments, the amount of the alkyl sulfate surfactant added to the composition can be from 0.05% (or about 0.05%) to 2.0% (or about 2.0%) w/v, or optionally from 0.1% (or about 0.1%) to 0.5% (or about 0.5%) w/v of the composition.

The total surfactant concentration should not exceed or should be less than 2% (or about 2%), optionally, the total surfactant concentration should not should not exceed or should be less than 1.5% (or about 1.5%), optionally, the total surfactant concentration should not should not exceed or should be less than 1.0% (or about 1.0%, optionally, the total surfactant concentration should not should not exceed or should be less than 0.5% (or about 0.5%).

Aqueous Phase

The first premix and the second premix are added to an aqueous phase comprising water to form oil-in-water or water-in-oil dispersions, micro emulsions or emulsions.

In certain embodiments, the aqueous phase comprises from about 60% to about 95%, or optionally from about 75% to about 93%, by weight of the composition.

Alternatively, the liquid or mouth rinse compositions of the present invention may be formulated in a dry powder, chewing gum, semi-solid, solid or liquid concentrate form. In such embodiments, for example, water is added to q.s. as necessary in the case of liquid concentrates or powdered formulations, or water may be removed using standard evaporation procedures known in the art to produce a composition in dry powder form. Evaporated, or freeze dried forms are advantageous for storage and shipping.

Sugar Alcohol Solvent

In certain embodiments, a sugar alcohol is also added to the liquid or mouth rinse compositions of the present invention. The sugar alcohol solvent(s) may be selected from those multi-hydroxy-functional compounds that are conventionally used in oral and ingestible products. In certain embodiments, the sugar alcohol (s) should be non-metabolized and non-fermentable sugar alcohol (s). In specific embodiments, the sugar alcohols include, but are not limited to sorbitol, xylitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. Optionally, the sugar alcohol is sorbitol.

In certain embodiments, the total amount of sugar alcohol (s), which are added to effectively aid in the dispersion or dissolution of the mouth rinse or other ingredients, should not exceed 20% w/v (or about 20% w/v) of the total composition. Optionally, total amount of sugar alcohol should not exceed 17% w/v (or about 17% w/v) of the total composition. Optionally, total amount of sugar alcohol should not exceed 10% w/v (or about 10% w/v) of the total composition. The sugar alcohol can be in an amount of from 1.0% (or about 1.0%) to 20.0% (or about 20.0%) w/v, optionally from 2.5% (or about 2.5%) to 17.0% (or about 17.0%) w/v, or optionally from 5.0% (or about 5.0%) to 15.0% (or about 15.0%) w/v of the total composition.

In certain embodiments, the ratio of the sugar alcohol to the total polyol solvent component in the composition should be from 10:1 (or about 10:10) to 1:10 (or about 1:10), optionally from 5:1 (or about 5:1) to 1:5 (or about 1:5), optionally 1:1 (or about 1:1) by weight.

In certain embodiments, the total amount of the solvent, including all polyol solvents and all sugar alcohol solvents, which is added to effectively aid in the dissolution or dispersion of the mouth rinse or other ingredients, should not exceed 47% w/v (or about 47% w/v) of the total composition. Optionally, total amount of solvent system should not exceed 20% w/v (or about 20% w/v) of the total composition. The solvent system can be in an amount of from 2% (or about 2%) to 47% (or about 47%) w/v, or optionally from 10% (or about 10%) to 20% (or about 20%) w/v of the total composition.

In certain embodiments, the ratio of the total solvent (i.e., polyol solvent and the sugar alcohol solvent) to the total surfactant in the composition should be from 360:1 (or about 360:1) to 10:1 (or about 10:1), optionally from 100:1 (or about 100:1) to 20:1 (or about 20:1) by weight.

Method of Manufacturing

Each of the above premixes is mixed until uniform and homogeneous. Once each premix is mixed until uniform and homogeneous, the first premix is added to the third premix and mixed until uniform and homogeneous. Once the mixture of the first premix and third premix are mixed until uniform and homogeneous, the second premix is added to the mixture of the first premix and third premix and mixed until uniform and homogeneous.

Without being limited by theory, it is believed that first oil or oily component and the second oil or oily component compete for the surfactant and solvents in the aqueous phase of the present invention. By first mixing the first oil or oily component of higher degree of hydrophobicity as a polyol solvent premix with an aqueous phase containing surfactant before adding a polyol solvent premix of the second oil or oily component of lower degree of hydrophobicity to the aqueous phase containing surfactant, the first oil or oily component of higher degree of hydrophobicity is mixed with the surfactant and/or solvent to achieve the dispersion and/or dissolution in the aqueous phase required to produce compositions having a turbidity of less than 12 (or about 12) Nephelometric Turbidity Units (NTUs). The turbidity of the liquid composition or mouth rinse is further reduced by adding any sugar alcohol solvents after the first and second oil or oily components have been added to an aqueous phase.

In certain embodiments, the liquid or mouth rinse compositions of the present invention have NTU values of less than 10 (or about 10), optionally 8 (or about 8), optionally 6 (or about 6), or optionally 4 (or about 4).

Optional Ingredients

Insoluble Particulates

In certain embodiments, the oral care compositions of the present invention optionally comprise a safe and effective amount of a water insoluble particulate. The water insoluble particulate can be an abrasive particle (such as a dentally acceptable abrasive) or non-abrasive particulate.

In certain embodiments, dentally acceptable abrasives include, but are not limited to, water insoluble calcium salts such as calcium carbonate, and various calcium phosphates, alumina, silica, synthetic resins and mixtures thereof. Suitable dentally acceptable abrasives may generally be defined as those having a radioactive dentine abrasion value (RDA) of from about 30 to about 250 at the concentrations used in the compositions of the present invention. In certain embodiments, abrasives are non-crystalline, hydrated, silica abrasives, particularly in the form of precipitated silica or milled silica gels available commercially, for example, under the trade names ZEODENT (J. M. Huber Corporation, Edison, N.J.), and SYLODENT (W.R. Grace & Co., New York, N.Y.), respectively. In certain embodiments, the compositions according to the present invention comprise from about 1% to about 20%, or, optionally, from about 5% to about 10% by weight of the abrasive.

Alternatively, the insoluble particulate is a non-abrasive particulate which is visible to the unaided eye and stable in the compositions of the present invention.

The non-abrasive particulate can be of any size, shape, or color, according to the desired characteristic of the product. The non-abrasive particulates will typically have the shape of a small round or substantially round ball or sphere, however, platelet or rod-shaped configurations are also contemplated herein. Generally, a non-abrasive particulate has an average diameter of from about 50 μm to about 5000 μm, optionally from about 100 μm to about 3000 μm, or optionally from about 300 μm to about 1000 μm. By the terms "stable" and/or "stability", it is meant that the abrasive or non-abrasive particulates are not disintegrated, agglomerated, or separated under normal shelf conditions. In certain embodiments, the terms "stable" and/or "stability" further mean that the compositions of present invention contain no visible or minimally visible (to the unaided eye) signs of sedimentation of the insoluble particulates after 8 weeks, optionally 26 weeks, optionally 52 weeks, at room temperature.

The non-abrasive particulates herein are typically incorporated in the present compositions at levels of from about 0.01% to about 25%, optionally, from about 0.01% to about 5%, or optionally, from about 0.05% to about 3%, by weight of the composition.

The non-abrasive particulate herein will typically comprise a structural material and/or, optionally, an encompassed material.

The structural material provides a certain strength to the non-abrasive particulates so that they retain their distinctively detectable structure in the compositions of the present invention under normal shelf conditions. In one embodiment, the structural material further can be broken and disintegrated with very little shear on the teeth, tongue or oral mucosa upon use.

The non-abrasive particulates can be solid or liquid, filled or un-filled, as long as they are stable in the compositions of the present invention. The structural material used for making the non-abrasive particulates varies depending on the compatibility with other components, as well as material, if any, to be encompassed in the non-abrasive particulates. Exemplary materials for making the non-abrasive particulates herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly (alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), allyl methacrylate, poly(ε-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. In certain embodiments, the components as described in this section form the structure of the non-abrasive particulates so as to not be substantially dissolved or dispersed from the particulates and into the compositions of the present invention under normal shelf conditions.

In other embodiments, the structural material herein comprises components selected from the group consisting of polysaccharides and their derivatives, saccharides and their derivatives, oligosaccharides, monosaccharides, and mixtures thereof, or optionally, comprises components are having various degrees of water solubility. In some embodiments, the structural material comprises lactose, cellulose, and hydroxypropyl methylcellulose.

Suitable non-abrasive particulates also include organogel particles as described in detail in U.S. Pat. No. 6,797,683. Non-abrasive particulates that are organogel particles typically comprise a structural material selected from waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted)sugars, dibenzyl sorbitol (or mannitoal, rabbitol, etc.), condensates and precondensates of lower monohydric alcohols, trihydroic alcohols, lower polyglycols, propylene/ethylene polycondensates, and the like. Optionally, structural material for non-abrasive particulates that are organogel particles include beeswax, carnauba wax, low molecular weight ethylene homopolymers (e.g. Polywax 500, Polywax 1000, or Polywax 2000 polyethylene materials available from Baker Petrolite Corp.), or paraffin wax.

The non-abrasive particulates herein may encompass, contain, or be filled with an encompassed material. Such encompassed material can be water soluble or water insoluble. Suitable encompassed materials include benefit agents as described herein such as: oral care actives, vitamins, pigments, dyes, antimicrobial agents, chelating agents, optical brighteners, flavors, perfumes, humectants, minerals, and mixtures thereof. The encompassed materials herein are substantially retained within the non-abrasive particulates, and are substantially not dissolved from the particulates and into the compositions of the present composition under normal shelf conditions.

Particularly useful commercially available non-abrasive particulates herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear and with practically no resistance, and readily disperse in the compositions of the present invention.

Suitable non-abrasive particulates for incorporation in the present compositions are described in detail in U.S. Pat. No. 6,797,683 (organogel particles); U.S. Pat. No. 6,045,813 (rupturable beads); U.S. 2004/0047822 A1 (visible capsules); and U.S. Pat. No. 6,106,815 (capsulated or particulated oily substances), each of which patent documents are herein incorporated by reference in their entirety.

In certain embodiments, the abrasive and/or nonabrasive particles have a density different or, optionally, substantially different from the carrier in which these particles are formulated.

Fluoride Releasing Compounds

In certain embodiments, fluoride providing compounds may be present in the mouth rinse compositions of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium hexafluorosilicate, ammonium hexafluorosilicate, sodium fluorozirconate, sodium monofluorophosphate, aluminum mono- and difluorophosphate and fluorinated sodium calcium pyrophosphate. Amine fluorides, such as N'-octadecyltrimethylendiamine-N,N,N'-tris(2-ethanol)-dihydrofluoride and 9-octadecenylamine-hydrofluoride), may also be used.

In certain embodiments, the fluoride providing compound is generally present in an amount sufficient to release up to 0.15% (or about 0.15%), optionally 0.001% (or about 0.001%) to 0.1% (or about 0.1%), optionally from 0.001% (or about 0.001%) to 0.05% (or about 0.05%) fluoride by weight of the composition.

Zinc Salts

In certain embodiments, zinc salts such as zinc chloride, zinc acetate or zinc citrate may be added as an astringent for an "antiseptic cleaning" feeling, as a breath protection enhancer or as anticalculus agent in an amount of from 0.0025% w/v (or about 0.0025% w/v) to 0.1% w/v (or about 0.1% w/v) of the composition.

Sensitivity Reducing Agents

In certain embodiments, sensitivity reducing agents, namely potassium salts of nitrate and oxalate in an amount from 0.1% (or about 0.1%) to 5.0% (or about 5.0%) w/v of the composition may be incorporated into the present invention. Other potassium releasing compounds are feasible (e.g. KCl). High concentrations of calcium phosphates may also provide some added sensitivity relief. These agents are believed to work by either forming an occlusive surface mineral deposit on the tooth surface or through providing potassium to the nerves within the teeth to depolarize the nerves. A more detailed discussion of suitable sensitivity reducing can be found in US 20060013778 to Hodosh and U.S. Pat. No. 6,416,745 to Markowitz et al., both of which are herein incorporated by reference in their entirety.

Anticalculus Agents

In certain embodiments, compounds with anti-calculus benefits (e.g. polyphosphates, phosphonates, various carboxylates, polyaspartic acid, inositol phosphate etc.) may be incorporated into the present invention. Also useful as an anticalculus agent are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 by weight copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Additional Ingredients

Although the liquid or mouth rinse compositions of the present invention may be formulated to be substantially clear and/or colorless to the unaided eye, acceptably approved food dyes are preferably used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from 0.00001% w/v (or about 0.00001% w/v) to 0.0008% w/v (or about 0.0008% w/v), optionally from 0.00035% w/v (or about 0.00035% w/v) to 0.0005% w/v (or about 0.0005% w/v) of the composition.

Other conventional ingredients may be used in the liquid or mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from 0.1% w/v (about 0.1% w/v) to 0.6% w/v (or about 0.6% w/v), optionally 0.5% w/v (or about 0.5% w/v) of the composition.

A more detailed description of useful oral care actives and/or inactive ingredients and further examples thereof can be found in U.S. Pat. No. 6,682,722 to Majeti et al. and U.S. Pat. No. 6,121,315 to Nair et al., each of which are herein incorporated by reference in its entirety.

In certain embodiments, the compositions of the present invention are free of or essentially free of bioavailability affecting compounds. As used herein, "bioavailability affecting compound", means compounds that negatively affect the bioavailability of any incorporated essential oils such as by binding the essential oils or otherwise inactivating the essential oils. "Essentially free" as used with respect to bioavailability affecting compounds is defined as formulations having less than 5% (or about 5%), optionally, 3% (or about 3%), optionally, 1% (or about 1%), or optionally 0.1, or optionally, 0.01% (or about 0.01%), by weight (w/v) of the total composition of a bioavailability affecting compound. In certain embodiments, the bioavailability affecting compound can include, but is not limited to, polyethylene oxide/polypropylene oxide block copolymers such as poloxamers; cyclodextrins; polysorbates such as Tweens; and mixtures thereof.

Methods of Practicing the Present Invention

The invention illustratively disclosed herein may be practiced in the absence of any component, ingredient, or step which is not specifically disclosed herein.

In certain embodiments, the compositions of the present invention are applied to teeth and/or soft surfaces of the oral cavity for at least two consecutive applications, optionally, at least (or greater than) 3 (or about 3) or optionally, at least (or greater than) 5 (or about 5) consecutive applications.

When applied to teeth and/or soft surfaces of the oral cavity, in certain embodiments, the composition is allowed to remain in contact with the teeth and/or soft surfaces of the oral cavity for at least (or greater than) 10 (or about 10) seconds, optionally 20 (or about 20) seconds, optionally 30 (or about 30) seconds, optionally 50 (or about 50) seconds, or optionally 60 (or about 60) seconds.

Various embodiments of the invention have been set forth above. Each embodiment is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

EXAMPLES

The following examples are illustrative only and should not be construed as limiting the invention in any way. Those skilled in the art will appreciate that variations are possible which are within the spirit and scope of the appended claims.

Example 1: Effect of Various Methods of Forming Formulations, and Increasing Surfactant Levels Nine propylene-glycol based mouth rinse formulations were prepared by a variety of methods using various surfactants that are approved for use in oral care products. The formulations were tested for turbidity and antimicrobial activity. Turbidity was tested using a Laboratory Turbidimeter Model 2100N from Hach Company (Loveland, Colo.). The formulations were also tested using an in-vitro single species *S. mutans* biofilm model. A 22-hour *S. mutans* biofilm was grown (N=96) and exposed to the formulations as well as positive and negative controls for 30 seconds. Sterile water was used as the negative control. After treatment the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and the ATP from the bacteria was measured using the bioluminescence marker Celsis LuminATE. Decreasing log RLUs (relative light units) indicates fewer bacteria alive after treatment. The nine formulations are shown on Table 1. Final formulations were adjusted to pH 4.2 with 0.1M NaOH or 0.1M HCl if necessary.

TABLE 1

| | Formulations | | | | | | | | | |
|---|---|---|---|---|---|---|---|---|---|---|
| Ingredients | 1A (% w/w) | 1B (% w/w) | 1C (% w/w) | 1D (% w/w) | 1E (% w/w) | 1F (% w/w) | 1G (% w/w) | 1H (% w/w) | 1I (% w/w) | Negative Control |
| Propylene glycol USP | 7.0 | 7.0 | 7.0 | 7.0 | 7.0 | 7.0 | 7.0 | 7.0 | 7.0 | — |
| L-Menthol USP | 0.0413 | 0.0413 | 0.0413 | 0.0413 | 0.0413 | 0.0413 | 0.0413 | 0.0413 | 0.0413 | — |
| Thymol NF | 0.0620 | 0.0620 | 0.0620 | 0.0620 | 0.0620 | 0.0620 | 0.0620 | 0.0620 | 0.0620 | — |
| Methyl salicylate NF | 0.0641 | 0.0641 | 0.0641 | 0.0641 | 0.0641 | 0.0641 | 0.0641 | 0.0641 | 0.0641 | — |
| Eucalyptol USP | 0.0895 | 0.0895 | 0.0895 | 0.0895 | 0.0895 | 0.0895 | 0.0895 | 0.0895 | 0.0895 | — |
| Flavor | 0.1000 | 0.1000 | 0.1000 | 0.1000 | 0.1000 | 0.1000 | 0.1000 | 0.1000 | 0.1000 | — |
| Sorbitol (70% solution) USP | 10.000 | 10.000 | 10.000 | 10.000 | 10.000 | 10.000 | 10.000 | 10.000 | 10.000 | — |
| Sodium Lauryl Sulfate USP | 0.3150 | 0.3150 | 0.3150 | — | — | 0.3150 | 0.3150 | 0.3150 | 0.3150 | — |
| Poloxamer 407 NF | — | — | — | 2.0000 | — | — | — | — | — | — |
| Tween 20 | — | — | — | — | 2.0000 | — | — | — | — | — |
| Sodium Saccharin USP | 0.0606 | 0.0606 | 0.0606 | 0.0606 | 0.0606 | 0.0606 | 0.0606 | 0.0606 | 0.0606 | — |
| Sucralose NF | 0.0100 | 0.0100 | 0.0100 | 0.0100 | 0.0100 | 0.0100 | 0.0100 | 0.0100 | 0.0100 | — |
| Benzoic Acid USP | 0.0859 | 0.0859 | 0.0859 | 0.0859 | 0.0859 | 0.0859 | 0.0859 | 0.0859 | 0.0859 | — |
| Sodium Benzoate | 0.0773 | 0.0773 | 0.0773 | 0.0773 | 0.0773 | 0.0773 | 0.0773 | 0.0773 | 0.0773 | — |

TABLE 1-continued

| | Formulations | | | | | | | | | |
|---|---|---|---|---|---|---|---|---|---|---|
| Ingredients | 1A (% w/w) | 1B (% w/w) | 1C (% w/w) | 1D (% w/w) | 1E (% w/w) | 1F (% w/w) | 1G (% w/w) | 1H (% w/w) | 1I (% w/w) | Negative Control |
| NF FD&C Green #3 | 0.00002 | 0.00002 | 0.00002 | 0.00002 | 0.00002 | 0.00002 | 0.00002 | 0.00002 | 0.00002 | — |
| Purified Water USP | QS | QS | QS | QS | QS | QS | QS | QS | QS | — |
| TOTAL | 100.0 | 100.0 | 100.0 | 100.0 | 100.0 | 100.0 | 100.0 | 100.0 | 100.0 | — |
| log RLU | 6.01 | 5.46 | 5.45 | 7.64 | 7.68 | 5.49 | 5.62 | 5.52 | 5.55 | 7.67 |
| M-factor | 1.66 | 2.21 | 2.22 | 0.03 | −0.01 | 2.18 | 2.05 | 2.15 | 2.12 | 0 |
| Turbidity (NTU) | 11.4 | 13.3 | 12.8 | 10.7 | 2.22 | 16.1 | 3.93 | 15.9 | 17.2 | |

The procedure for mixing the formulations was as follows:

Formulation 1A: The water was put in an appropriately sized tank (or vessel), then all remaining ingredients were added to the water and mixed until dispersed. No separate premixes were formed.

Formulation 1B: In step 1, the polyol solvent (i.e., propylene glycol) was put in an appropriately sized tank (or vessel). The active oils and flavor were added to the polyol solvent in the tank and mixed until homogeneous and uniform to form a premix. In step 2, instead of adding as the final component in the final step of the formulation process, the sugar alcohol was added to the premix and mixed until the formulation was homogeneous and uniform before adding the surfactant, water, organic acid buffer, preservative, sweeteners and dyes. In step 3, the surfactant was added to the premix and mixed until the formulation was homogeneous and uniform. In step 4, the water was added to the premix and mixed until the formulation was homogeneous and uniform. In step 5, the organic acid buffer, preservative, and sweeteners were added to the premix, and mixed until homogeneous and uniform. In step 6, the dye was added to the premix and mixed until the formulation was homogeneous and uniform.

Formulations 1C, 1D, and 1E: In step 1, the polyol solvent (i.e., propylene glycol) was put in an appropriately sized tank (or vessel). The organic acid buffer was added to the polyol solvent to form a first premix and mixed until homogeneous and uniform. In step 2, instead of forming a second premix of active oil and a second polyol solvent and adding the second premix to a third premix comprising water, surfactant, preservative and sweetener, the active oils and flavor were added directly to the first premix and mixed until homogeneous and uniform. In step 3, the sugar alcohol co-solvent was added to the first premix and mixed until the formulation was homogeneous and uniform. In step 4, the surfactant was added to the first premix and mixed until the formulation was homogeneous and uniform. In step 5, the water, sweeteners, and preservative were added to the first premix, and mixed until homogeneous and uniform. In step 6, the dye was added to the first premix and mixed until the formulation was homogeneous and uniform. In Formulations 1D and 1E, higher levels of surfactant were added, when compared to Formulation 1C.

Formulation 1F: In step 1, in a first appropriately sized tank (or vessel), a first premix was formed by adding 5% first polyol solvent (i.e., propylene glycol) to active oils and flavor and mixed until they were homogeneous and uniform. In step 2, in a second appropriately sized tank (or vessel), a second premix was formed by adding 2.0% second polyol solvent which was the same as the first polyol solvent to an organic acid buffer and mixed in the second tank until homogeneous and uniform. In step 3, instead of adding as the final component in the final step of the formulation process, the sugar alcohol solvent was added and mixed directly into the first premix until homogeneous and uniform before adding the surfactant, water, preservative, sweeteners and dyes. In step 4, the surfactant was added and mixed into the first premix until the formulation was homogeneous and uniform. In step 5, the water was added and mixed into the first premix until the formulation was homogeneous and uniform. In step 6, the second premix was added to the first premix and mixed until the formulation was homogeneous and uniform. In step 7, the preservative and sweeteners were added, and mixed until homogeneous and uniform. In step 8, the dye was added and mixed until the formulation was homogeneous and uniform.

Formulation 1G (using the inventive process): In step 1, in a first appropriately sized tank (or vessel), a premix was formed by adding 5.0% first polyol solvent (i.e., propylene glycol), active oils and flavor and mixed until homogeneous and uniform. In step 2, in a second appropriately sized tank (or vessel), a second premix was formed by adding to an organic acid buffer 2.0% second polyol solvent which was the same as the first polyol solvent and mixed until homogeneous and uniform. In step 3, in a third appropriately sized tank (or vessel), a third premix was formed by adding surfactant, preservative and sweeteners to water and mixing until homogeneous and uniform. In step 4, the first premix was added to the third premix and mixed until homogeneous and uniform. In step 5, the second premix was added to the mixture of the first and third premixes and mixed until homogeneous and uniform. In step 6, the dye was added to the mixture of the three premixes and mixed until homogeneous and uniform. In step 7, the sugar alcohol was added as the final component to the mixture of the three premixes and mixed until the final mixture was homogeneous and uniform.

Formulation 1H: In step 1, in a first appropriately sized tank (or vessel), instead of forming separate premixes (one premix containing the active oils and the other premix containing the organic acid buffer), a first premix was formed by adding both organic acid buffer and active oils to a polyol solvent (i.e., propylene glycol) and flavor and mixing until homogeneous and uniform. In step 2, in a second appropriately sized tank (or vessel), instead of adding as the final component in the final step of the formulation process, the sugar alcohol solvent was added to surfactant, preservative, sweeteners and water and mixed until homogeneous and uniform to form a second premix. In step 3, the first premix was added to the second premix and mixed until homogeneous and uniform. In step 4, the dye was added to the mixture of the two premixes and mixed until homogeneous and uniform.

Formulation 1I: In step 1, in a first appropriately sized tank (or vessel), a first premix was formed by adding 5.0% first polyol solvent (i.e., propylene glycol) to active oils and flavor and mixed until homogeneous and uniform. In step 2, in a second appropriately sized tank (or vessel), a second premix was formed by adding 2.0% second polyol solvent which was the same as the first polyol solvent to an organic acid buffer and mixed until homogeneous and uniform. In step 3, a third appropriately sized tank (or vessel), a third premix was formed by adding surfactant, sorbitol, preservative and sweeteners water and mixing until homogeneous and uniform. In step 4, instead of adding the first premix to the third premix, the second premix was added to the third premix and mixed until homogeneous and uniform. In step 5, the first premix is added to the mixture of the second premix and third premix and mixed until homogeneous and uniform. In step 6, the dye was added and mixed until uniform.

In addition to the listing the formulation ingredients, Table 1 shows the results of the turbidity test, in Nephelometric Turbidity Units (NTU), and *S. mutans* biofilm kill tests, in log RLU and M-Factor units. A typical M-factor for a commercially available alcohol containing essential oil mouth rinse is about 1.87 (log RLU of 5.8) in this model.

Table 1 also shows that all formulations containing sodium lauryl sulfate (Formulations 1A, 1B, 1C and 1F through 1I) displayed high biocidal activity (M-factor between 1.66 and 2.22). However, the turbidity of all of three sodium lauryl sulfate formulations (1A, 1B, and 1C) was high (NTU greater than about 10.5). When the total surfactant concentration level was raised to 2.0% (Formulations 1D and 1E), the turbidity improved, however, at such a high surfactant concentration level, the biocidal activity, as measured by M-factor, decreased substantially (M-factor=0.03 and −0.01, respectively). Only the formulation formed by the inventive processes of the present invention (Formulation 1G) provided both good efficacy (M-factor=2.05) and the lowest turbidity (NTU less than 4.0).

What is claimed is:

1. A composition comprising:
   a. polyol solvent selected from the group consisting of polyhydric alkanes, polyhydric alkane esters, polyalkene glycols, and mixtures thereof;
   b. sugar alcohol solvent selected from the group consisting of sorbitol, xylitol, mannitol, maltitol, inositol, allitol, altriol, dulcitol, galactitol, glucitol, hexitol, iditol, pentitol, ribitol, erythritol, and mixtures thereof;
   c. surfactant selected from the group consisting of anionic surfactants, nonionic surfactants, amphoteric surfactants and mixtures thereof;
   d. organic acid selected from the group consisting of benzoic acid, sorbic acid, succinic acid, citric acid, and mixtures thereof;
   e. one or more antimicrobial essential oils; and
   f. water;
   wherein said composition is free of $C_2$-$C_4$ monohydric alcohols and further wherein said composition free of poloxamers wherein said one or more antimicrobial essential oils are selected from the group consisting of menthol, thymol, eucalyptol, methyl salicylate and mixtures thereof.

2. The composition of claim 1 wherein said polyol solvent comprises propylene glycol.

3. The composition of claim 1 wherein said sugar alcohol solvent comprises sorbitol.

4. The composition of claim 1 wherein said surfactant comprises sodium lauryl sulfate.

5. The composition of claim 1 wherein said organic acid comprises benzoic acid.

6. The composition of claim 1 comprising propylene glycol and sorbitol.

7. The composition of claim 6 further comprising sodium lauryl sulfate.

8. The composition of claim 1 wherein said surfactant is a nonionic surfactant selected from alkyl polyglucosides; ethoxylated hydrogenated castor oils; alkyl polyethylene oxide; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

9. The composition of claim 1 wherein said surfactant is an amphoteric surfactant selected from alkylimino-diproprionates; alkylamphoglycinates, mono or di; alkylamphoproprionates, mono or di; alkylamphoacetates, mono or di; N-alkyl P-aminoproprionic acids; alkylpolyamino carboxylates; phosphorylated imidazolines; alkyl betaines; alkylamido betaines; alkylamidopropyl betaines; alkyl sultaines; alkylamido sultaines; and mixtures thereof.

* * * * *